US009283003B2

(12) United States Patent
Iott et al.

(10) Patent No.: US 9,283,003 B2
(45) Date of Patent: Mar. 15, 2016

(54) ORTHOPEDIC CLAMP AND EXTENSION ROD

(71) Applicant: Globus Medical, Inc., Audubon, PA (US)

(72) Inventors: Andrew Iott, Villanova, PA (US); Adam Friedrich, Cinnaminson, NJ (US); Douglas Cahill, Lititz, PA (US); Brad Juchno, Yardley, PA (US); Mark Salzberger, Sinking Spring, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 14/508,178

(22) Filed: Oct. 7, 2014

(65) Prior Publication Data
US 2015/0025584 A1    Jan. 22, 2015

Related U.S. Application Data

(63) Continuation of application No. 12/416,175, filed on Apr. 1, 2009, now Pat. No. 8,882,803.

(51) Int. Cl.
*A61B 17/88* (2006.01)
*A61B 17/70* (2006.01)

(52) U.S. Cl.
CPC .................................. *A61B 17/705* (2013.01)

(58) Field of Classification Search
CPC ............. A61B 17/705; A61B 17/7049; A61B 17/7052; A61B 17/88; A61B 17/7001; A61B 17/7005; A61B 17/7007; A61B 17/7008
See application file for complete search history.

(56) References Cited

U.S. PATENT DOCUMENTS

| | | | |
|---|---|---|---|
| D301,832 S | 6/1989 | Hathaway |
| 4,875,471 A | 10/1989 | Lea Plaza |
| 5,002,542 A | 3/1991 | Frigg |
| 5,176,680 A | 1/1993 | Vignaud |
| 5,209,752 A | 5/1993 | Ashman |
| 5,306,275 A | 4/1994 | Bryan |
| 5,366,455 A | 11/1994 | Dove |
| 5,466,237 A | 11/1995 | Byrd et al. |
| 5,609,592 A | 3/1997 | Brumfield et al. |
| 5,743,911 A | 4/1998 | Cotrel |
| 5,961,516 A | 10/1999 | Graf |
| 6,004,322 A | 12/1999 | Bernstein |
| 6,086,588 A | 7/2000 | Ameil et al. |
| 6,187,005 B1 | 2/2001 | Brace et al. |
| 6,485,491 B1 | 11/2002 | Farris et al. |
| 6,565,567 B1 | 5/2003 | Haider |
| 6,660,004 B2 | 12/2003 | Barker et al. |
| 6,733,502 B2 | 5/2004 | Altarac et al. |
| 7,166,109 B2 | 1/2007 | Biedermann et al. |
| 7,699,872 B2 | 4/2010 | Farris |
| D622,395 S | 8/2010 | Iott |

(Continued)

*Primary Examiner* — Jacqueline Johanas

(57) ABSTRACT

Spinal implants and methods of extending pre-existing spinal implant constructs. An extension clamp may be connected to an original spinal implant including an elongated rod attached to a portion of the spine without removal of the original spinal implant. The extension clamp may include a yoke and an extension rod extending from the yoke. The yoke may include a first end and a second end, the first end having first and second rod engaging portions and a channel between the first and second rod engaging portions for encompassing a fastener, and the second end being spaced apart from the first end. The first and second rod engaging portions may be configured and dimensioned to secure the extension clamp to the elongated rod.

14 Claims, 8 Drawing Sheets

(56) References Cited

U.S. PATENT DOCUMENTS

| | | | |
|---|---|---|---|
| 7,867,255 B2 * | 1/2011 | Miller | A61B 17/705 606/250 |
| 7,947,066 B2 * | 5/2011 | Tepper | A61B 17/7052 606/278 |
| 8,021,399 B2 | 9/2011 | Ritland | |
| 8,162,986 B2 * | 4/2012 | Zehnder | A61B 17/7004 606/257 |
| 8,419,773 B2 * | 4/2013 | Biedermann | A61B 17/7031 606/259 |
| 8,882,803 B2 * | 11/2014 | Iott | A61B 17/705 606/246 |
| 2002/0052603 A1 * | 5/2002 | Nichols | A61B 17/7052 606/914 |
| 2004/0153070 A1 | 8/2004 | Barker | |
| 2004/0254577 A1 | 12/2004 | Delecrin | |
| 2005/0010215 A1 | 1/2005 | Delecrin | |
| 2005/0137594 A1 | 6/2005 | Doubler | |
| 2005/0182409 A1 | 8/2005 | Callahan et al. | |
| 2005/0234451 A1 | 10/2005 | Markworth | |
| 2006/0009766 A1 | 1/2006 | Lee | |
| 2006/0079872 A1 | 4/2006 | Eggleston | |
| 2006/0079892 A1 | 4/2006 | Roychowdhury | |
| 2006/0084989 A1 | 4/2006 | Dickinson et al. | |
| 2006/0106380 A1 | 5/2006 | Colleran et al. | |
| 2006/0129149 A1 | 6/2006 | Iott | |
| 2006/0129239 A1 | 6/2006 | Kwak | |
| 2006/0149244 A1 | 7/2006 | Amrein et al. | |
| 2007/0043355 A1 | 2/2007 | Bette et al. | |
| 2007/0043365 A1 | 2/2007 | Ritland | |
| 2007/0233089 A1 | 10/2007 | DiPoto | |
| 2007/0233090 A1 | 10/2007 | Naifeh | |
| 2007/0233091 A1 | 10/2007 | Naifeh | |
| 2007/0270805 A1 | 11/2007 | Miller | |
| 2008/0009862 A1 | 1/2008 | Hoffman | |
| 2008/0045955 A1 | 2/2008 | Berrevoets et al. | |
| 2008/0058805 A1 * | 3/2008 | Stuart | A61B 17/7005 606/914 |
| 2008/0086126 A1 * | 4/2008 | Miller | A61B 17/705 606/86 R |
| 2008/0215095 A1 * | 9/2008 | Biedermann | A61B 17/7031 606/246 |
| 2008/0249570 A1 | 10/2008 | Carson et al. | |
| 2008/0262553 A1 | 10/2008 | Hawkins | |
| 2008/0294197 A1 | 11/2008 | Egli | |
| 2008/0294203 A1 | 11/2008 | Kovach et al. | |
| 2009/0036924 A1 * | 2/2009 | Egli | A61B 17/705 606/246 |
| 2009/0043339 A1 | 2/2009 | Tepper | |
| 2009/0093843 A1 | 4/2009 | Lemoine | |
| 2009/0118765 A1 | 5/2009 | Muller | |
| 2009/0182376 A1 | 7/2009 | Iott | |
| 2009/0210007 A1 | 8/2009 | Levy | |
| 2009/0228043 A9 | 9/2009 | Egli | |
| 2010/0036425 A1 | 2/2010 | Barrus | |
| 2010/0114167 A1 * | 5/2010 | Wilcox | A61B 17/7004 606/250 |
| 2010/0249843 A1 | 9/2010 | Wegrzyn | |
| 2010/0292736 A1 * | 11/2010 | Schwab | A61B 17/705 606/278 |
| 2012/0010664 A1 | 1/2012 | Ritland | |

* cited by examiner

ORTHOPEDIC CLAMP AND EXTENSION ROD

CROSS-REFERENCE TO RELATED APPLICATIONS

This application is a continuation of U.S. application Ser. No. 12/416,175 filed Apr. 1, 2009, the contents of which are incorporated by reference herein in its entirety for all purposes.

All publications and patent applications mentioned in this specification are herein incorporated by reference to the same extent as if each individual publication or patent application was specifically and individually indicated to be incorporated by reference.

FIELD OF THE INVENTION

The present invention relates to a spinal implant that stabilizes and supports the spine.

BACKGROUND OF THE INVENTION

Spinal deformities, spinal injuries, and other spinal conditions may be treated with the use of spinal implants. Spinal implants are designed to support the spine and properly position the components of the spine. One such spinal implant includes an elongated rod and a plurality of bone anchors. The elongated rod is positioned to extend along one or more of the components of the spine and the bone anchors are attached to the spinal components at one end and secured to the elongated rod at the other end.

However, adjacent segment disease and other conditions may require revisions requiring a surgeon to remove the entire spinal implant and position new implants to further support and stabilize the spinal components of the anatomy. The removal of the original spinal implant and the subsequent positioning of new implants may cause additional problems for the patient and increases the cost and time of spinal surgeries. Therefore, there is a need to provide spinal implants that provide support and stability to the spinal components of the anatomy by reducing the cost and time of the surgery caused by adjacent segment disease and other similar conditions.

Specifically, there is a need for a spinal implant that enables fusion and stability of the spine without removing the original implants, thereby reducing the time and cost of the surgery.

SUMMARY OF THE INVENTION

The present invention provides a spinal implant for connecting to an elongated rod. The spinal implant includes a yoke having a first end and a second end, the first end having a first and second rod engaging portion and a channel between the first and second rod engaging portions for encompassing a first bone anchor, and the second end being spaced apart from the first end. An extension rod is also provided which extends from the second end of the yoke parallel to the elongated rod. The first and second rod engaging portions are configured and dimensioned to receive first and second securing member for securing the elongated rod.

BRIEF DESCRIPTION OF THE DRAWINGS

The invention will be more readily understood with reference to the embodiments thereof illustrated in the attached drawing figures, in which.

DETAILED DESCRIPTION OF THE INVENTION

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Figure 1:
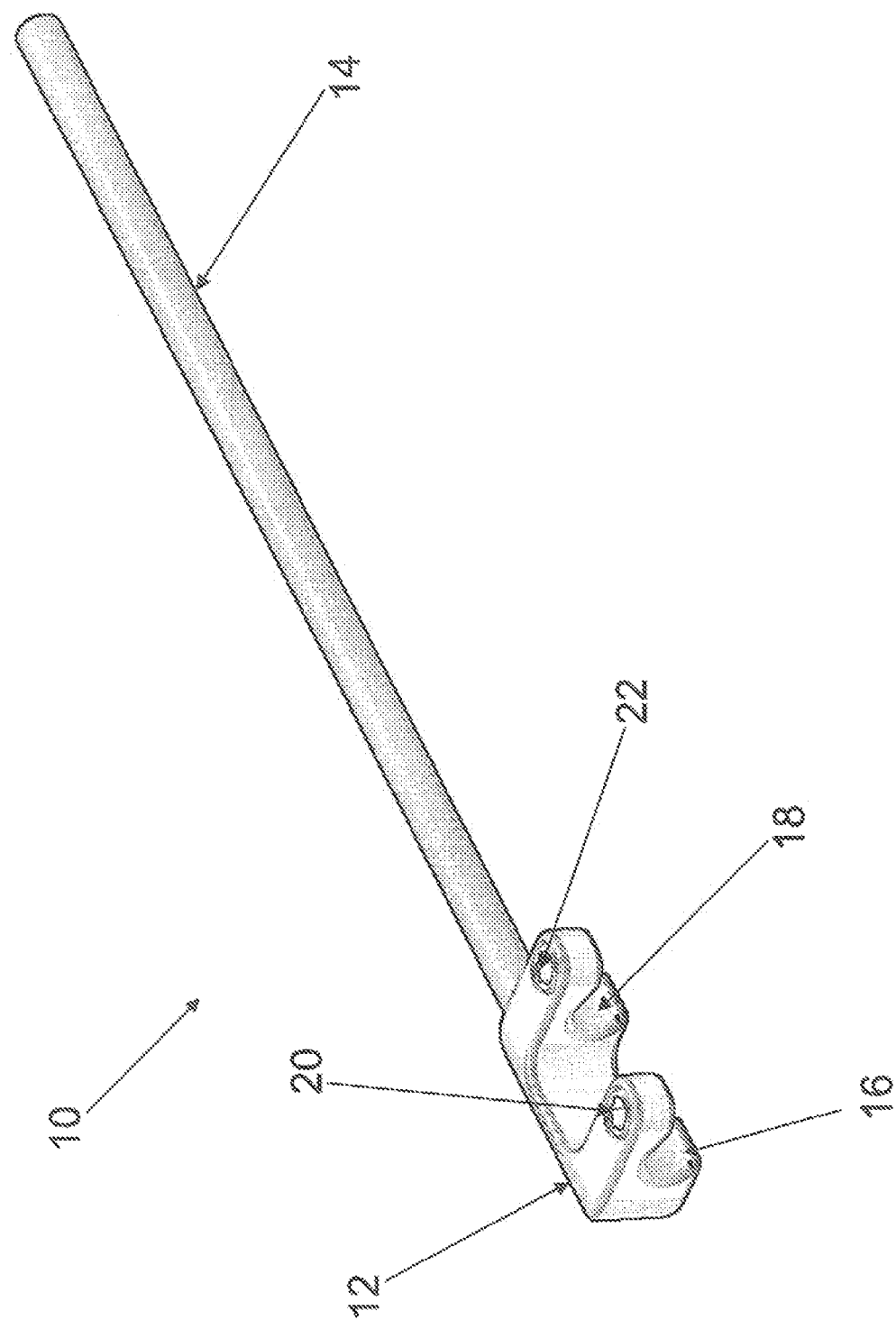
FIG. 1 illustrates the spinal implant according to the present invention.
Figure 2:
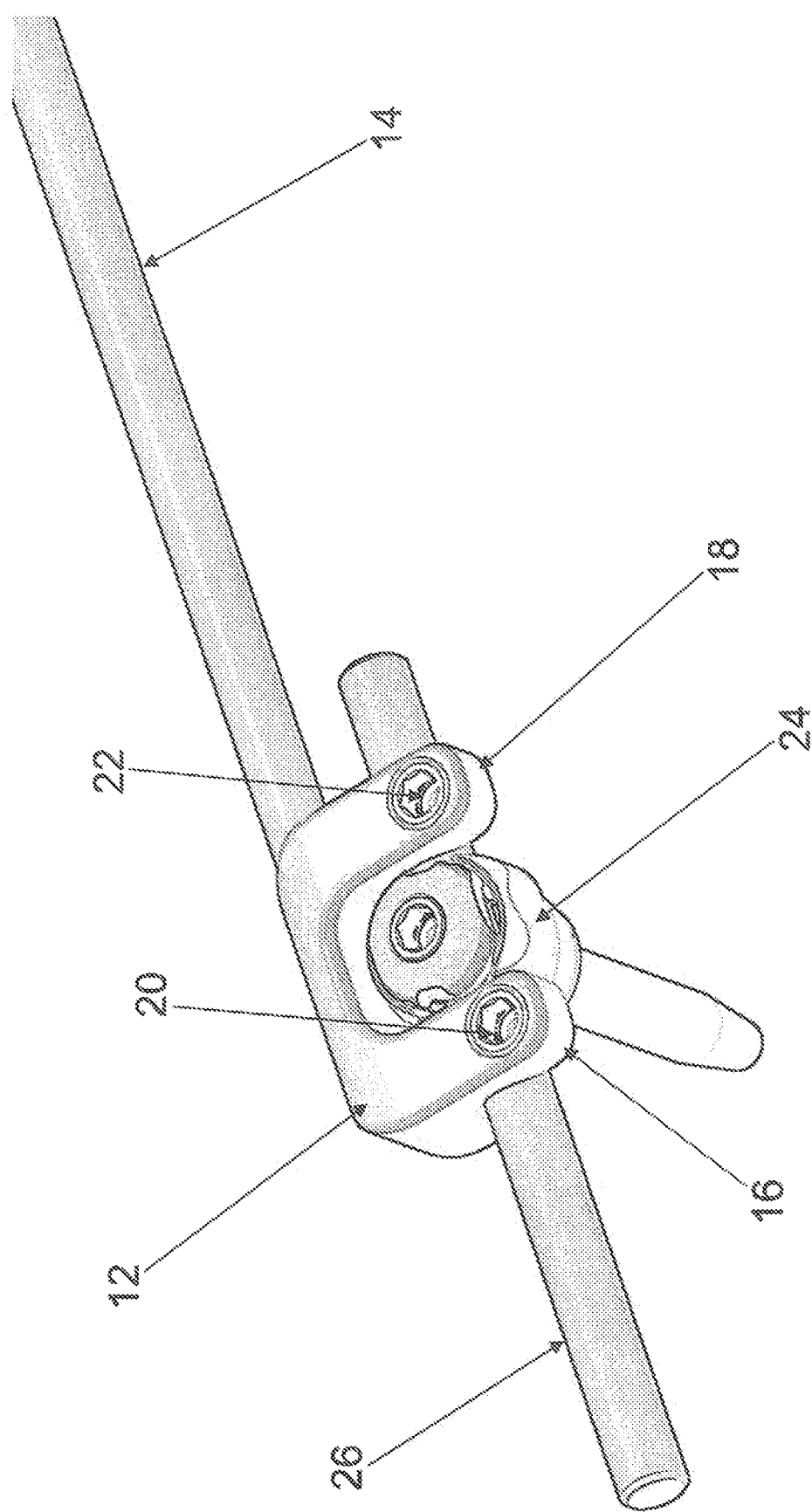
FIGS. 2-5 illustrate different views of the spinal implant in combination with a rod and screw system.
Figure 3:
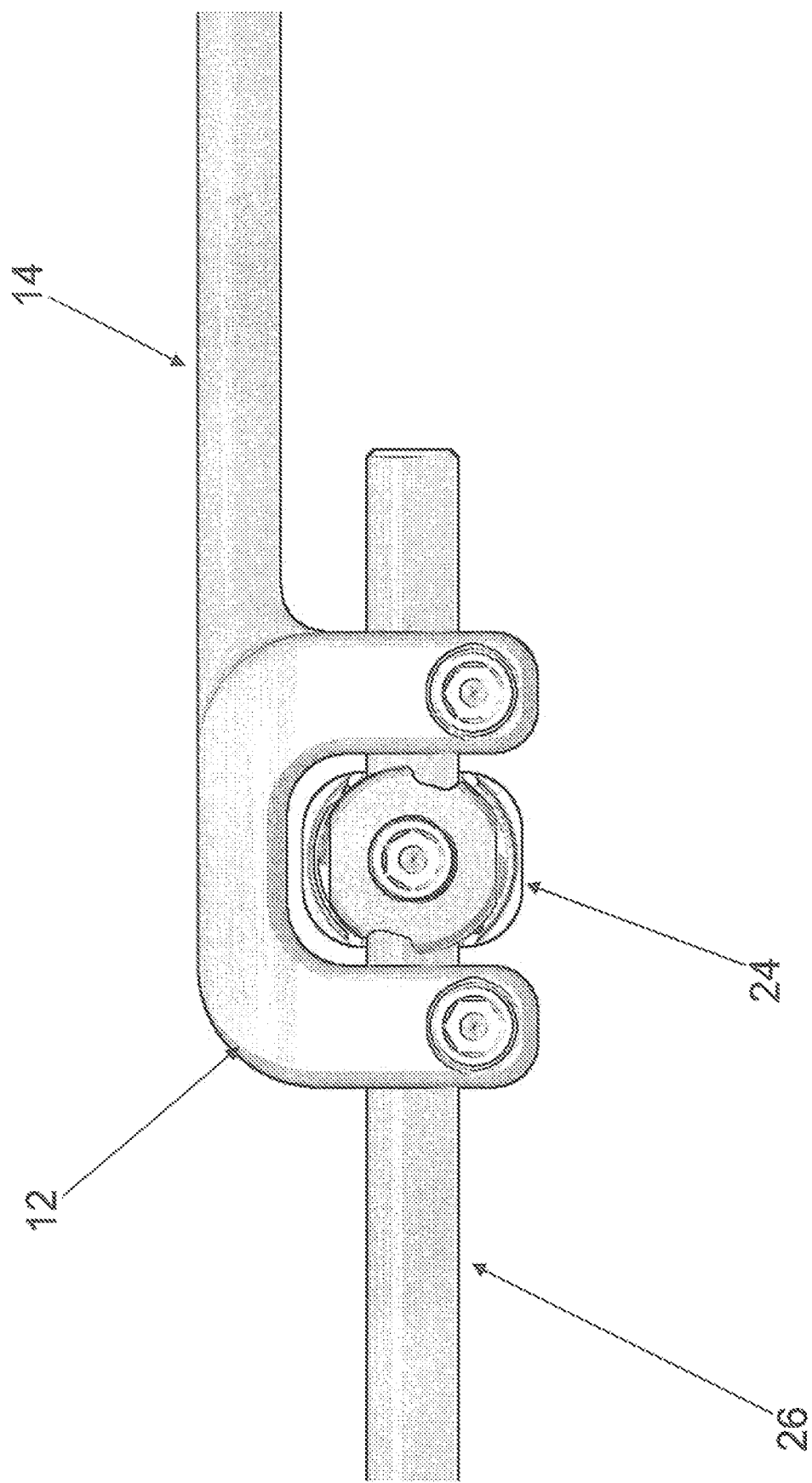
Figure 4:
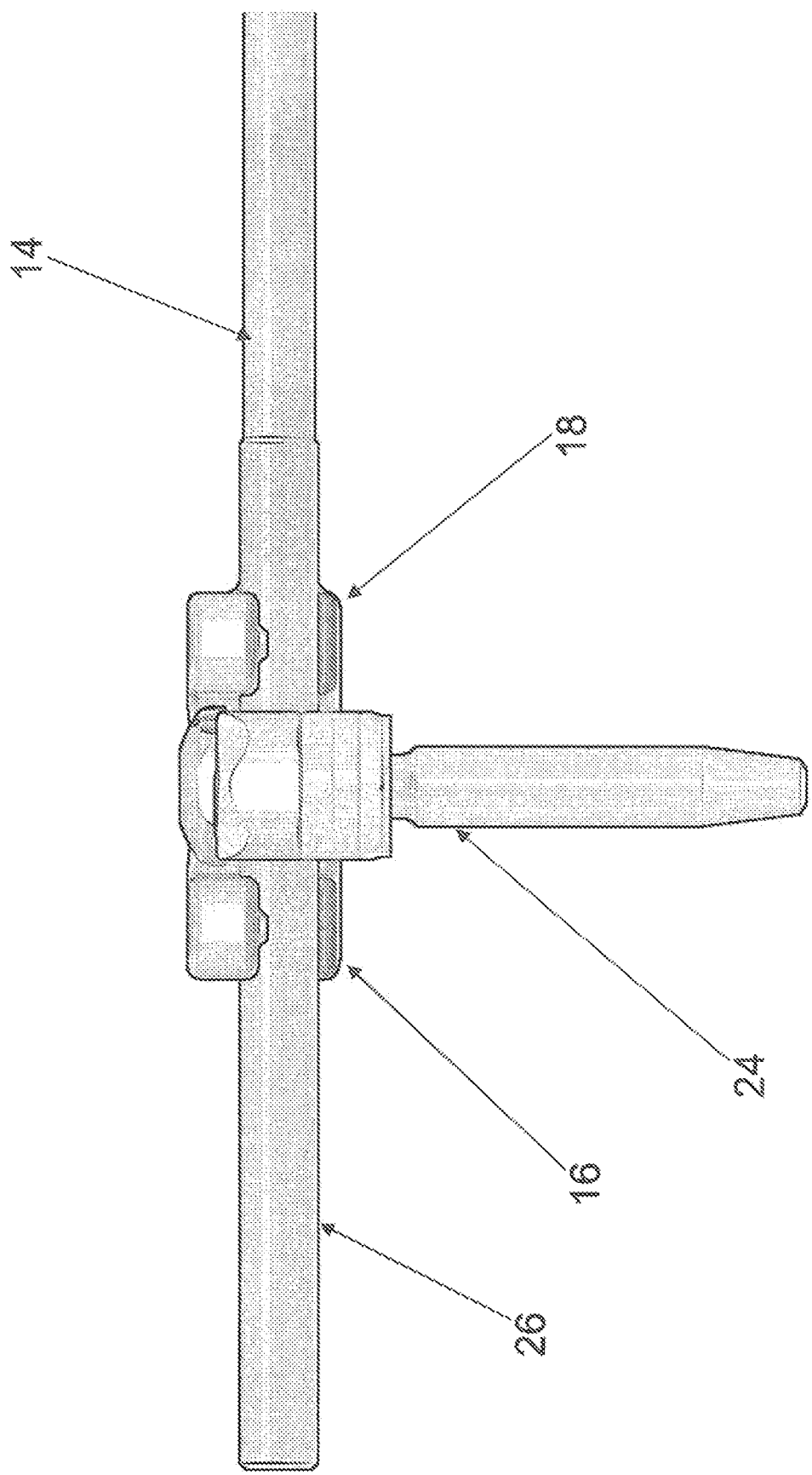
Figure 5:
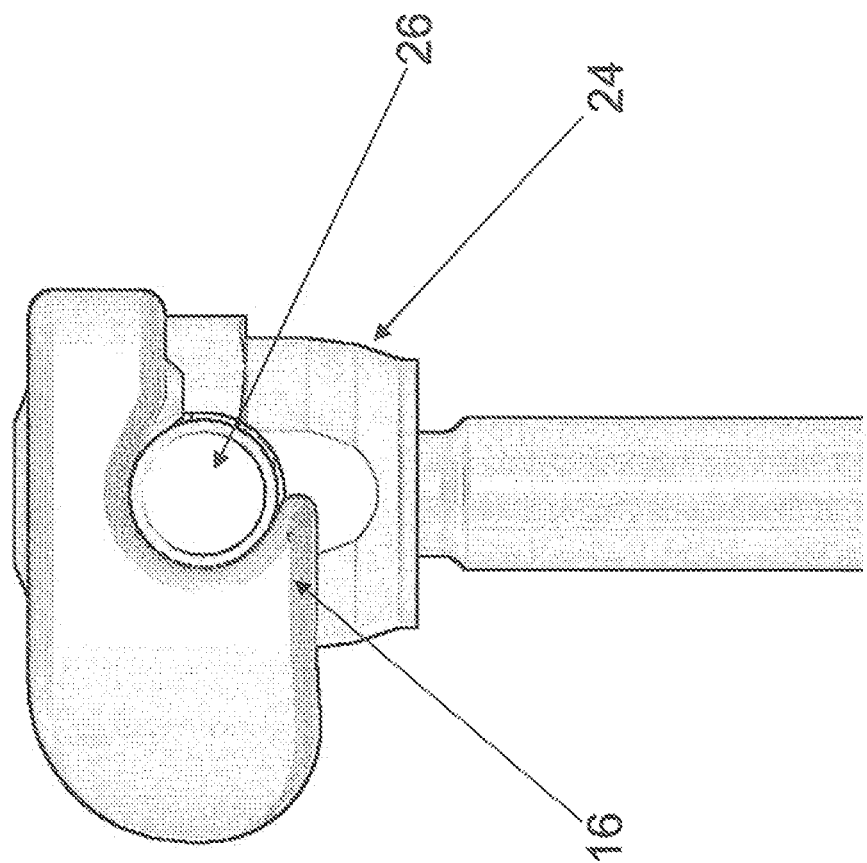
Figure 6:
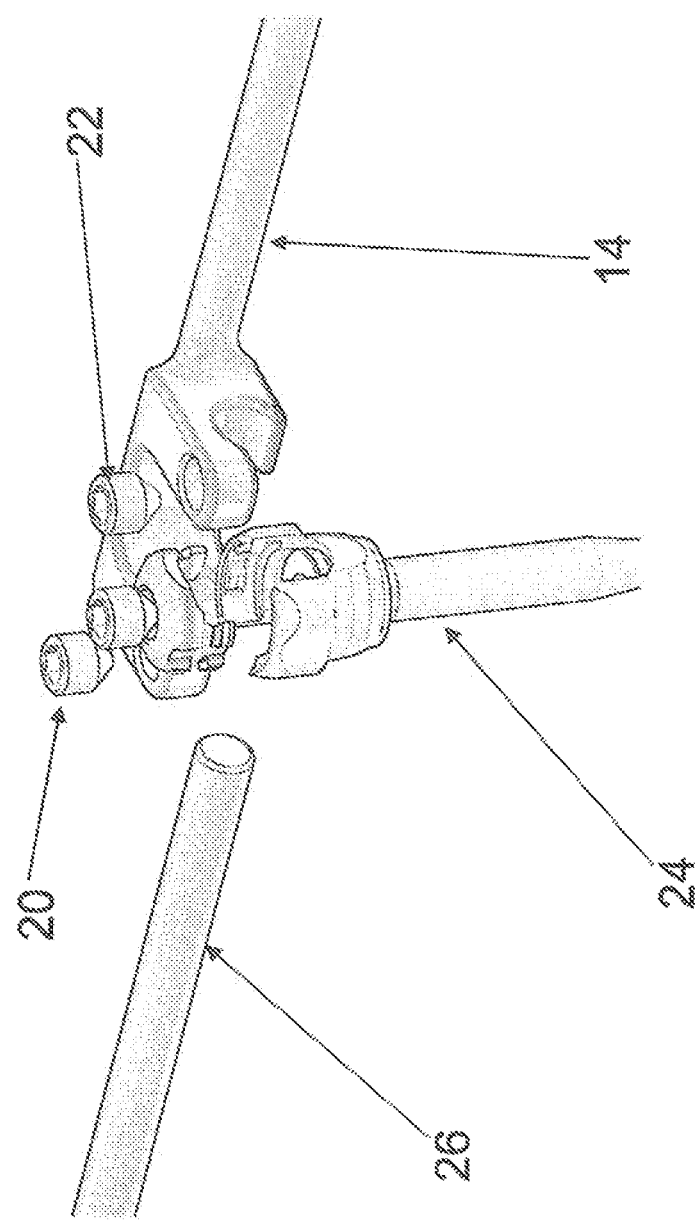
FIG. 6 is an exploded view of the implant system according to the present invention.

FIG. 1 illustrates the extension clamp 10 according to one embodiment of the present invention. The clamp 10 as shown is configured and dimensioned having a yoke 12 and an integrated rod 14. As clearly illustrated in FIG. 1, the yoke 12 and the rod 14 of the clamp 10 are integrated as a single piece. The yoke 14 is merged or integrated with the rod 12 that is preferably 160 millimeters long and having a diameter of 5.5 millimeters. However, the rod 12 may be shaped and sized to fit a patient's anatomy and any requirements to enhance the stability of the fusion fixation system. The clamp 10 is configured to connect to a rod and screw system as illustrated in FIGS. 2-6. The yoke 12 of the clamp 10 is also configured with a first and second rod engaging portions 16 and 18 for engaging with the rod. Each of the first and second rod engaging portions 16 and 18 are provided with first and second securing members 20, 22 for locking the clamp 10 onto the rod. The channel between the first and second rod engaging portions is dimensioned to encompass a fastening element such as a bone anchor or pedicle screw, which is more clearly illustrated in FIGS. 2-6.

Figure 7:
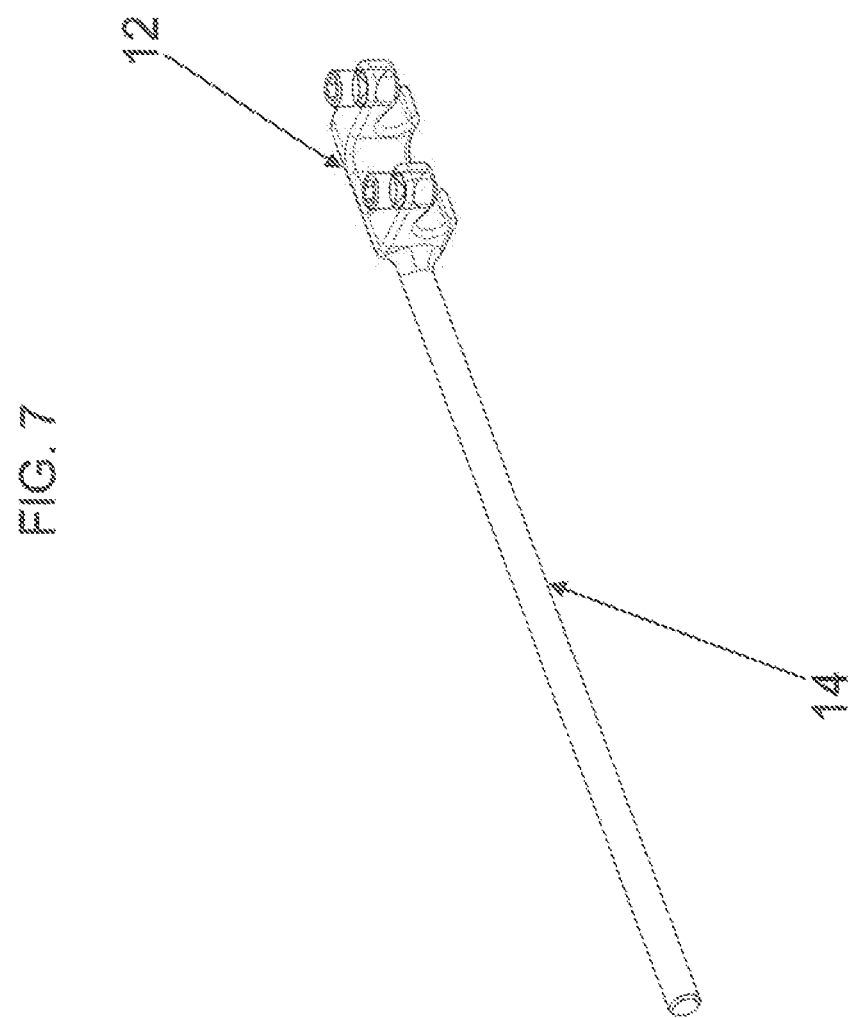
FIG. 7 illustrates another embodiment of the present invention.

FIGS. 2-6 illustrate the connection of the extension clamp 10 to a fastener/screw 24 and rod 26. As shown in FIGS. 2-6, the first and second engaging portions 16 and 18 of the yoke 12 engages with rod 26. The bone anchor which is attached to the honey elements of the spine and which captures and retains the rod 26 is fit within the channel of the yoke 12. The yoke 12 encompasses the bone anchor and secured to the rod 26 through the first and second securing members 20, 22. The clamp 10 being connected to the rod 26 and surrounding the bone fastener provides additional stability to the spine since the integrated rod 14 of the clamp 10 is attached to a bone element of the spine at an adjacent level segment through an another bone anchor. The integrated rod 14 as shown is spaced apart from the rod 26 that is coupled to the yoke 12 of the clamp 10. The integrated rod 14 is in a parallel axis to the connected rod 26. In this particular embodiment, the integrated rod 14 is illustrated to extend from one end of the clamp 10 spaced apart from the yoke 12. However, the integrated rod can be configured in various different designs, such as the integrated rod 14 extending from the a second end of the clamp spaced apart from the yoke as illustrated in FIG. 7.

Although a set screw is illustrated for coupling the clamp with the rod 26, any type of securing member can be used including, but not limited to, a bolt, a pin, a shoe, an interference member, or a cam member. In an exemplary embodiment, the securing member includes a coupling for engaging a driver or other device for threading the securing member into the second opening.

The integrated rod 14 is configured and dimensioned to be received and captured by a fastener which is attached to a pedicle or another bony element of the spine. The system allows a surgeon to reduce the amount of time in surgery as well as providing additional stability and support when enhancing fusion between vertebrae.

Figure 8:
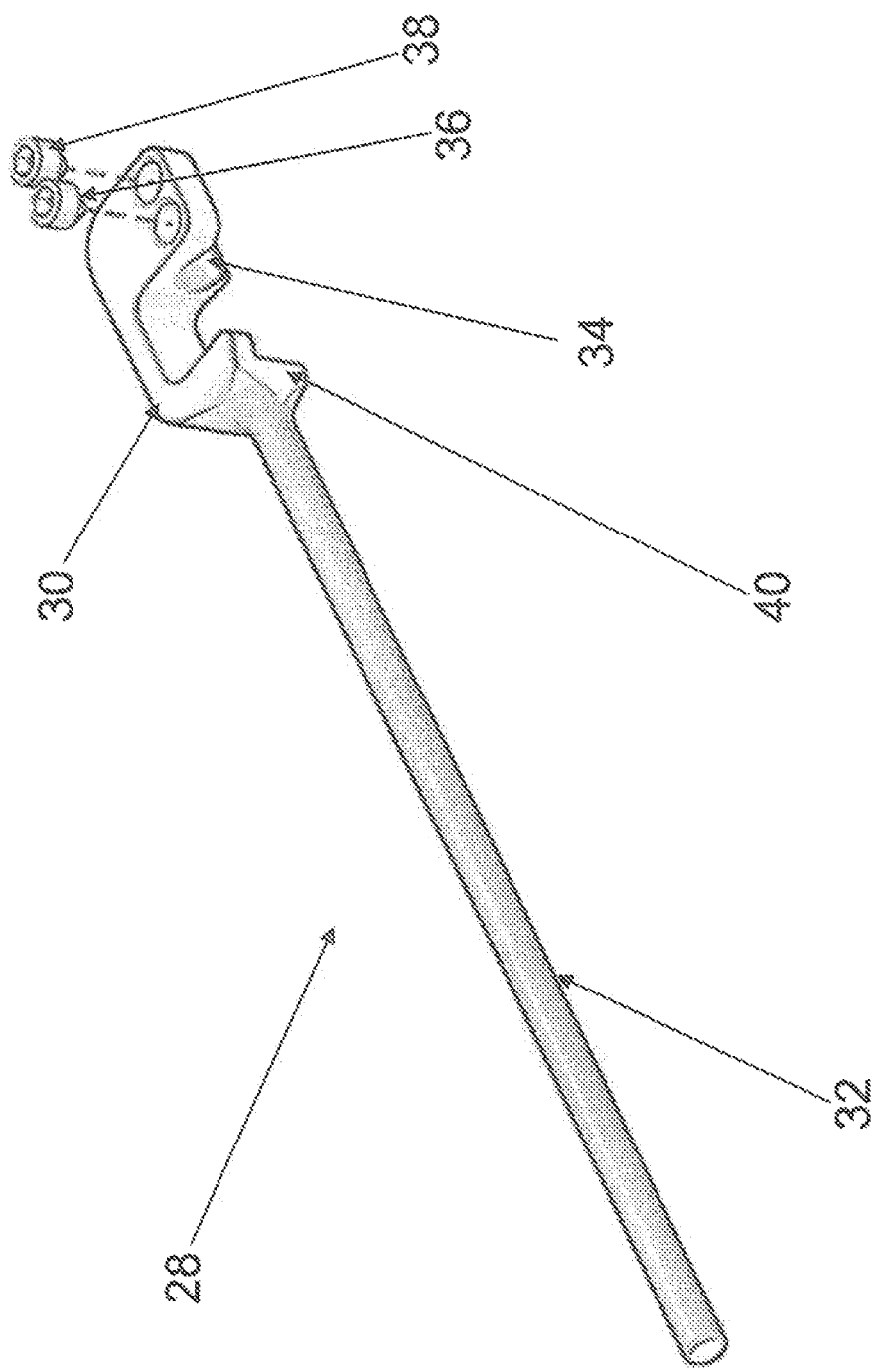
FIG. 8 illustrates yet another embodiment of the present invention.

FIG. 8 illustrates another embodiment of the present invention. In this particular embodiment, the clamp 28 is configured and dimensioned to be attached to a rod in in-line axis. The clamp 28 is provided with a yoke 30 and an inline integrated rod 32. The clamp 28 is secured to a rod (not shown) by the rod engaging portion 34 of the yoke 30. The yoke 30 is secured to the rod through securing members 36 and 38. One end of the rod is situated at the other end 40 of the yoke 30. As noted above, any type of securing element may be used to secure the rod to the clamp according the present invention.

Example embodiments having the components of the present invention have been described herein. As noted, these example embodiments having been described for illustrative purposes only, and are not limiting. Other embodiments are possible and are covered by the invention. Such embodiments will be apparent to persons skilled in the relevant art based on the teachings contained herein. Thus, the breadth and scope of the present invention should not be limited by any of the above-described exemplary embodiments, but should be defined only in accordance with the following claims and their equivalents.

What is claimed is:

1. A method of extending a pre-existing spinal implant construct including an elongated rod attached to a portion of the spine, the method comprising:
   providing an extension clamp including a monolithic yoke having a first end and a second end, the first end comprising first and second rod engaging portions and a channel between the first and second rod engaging portions, the second end being spaced apart from the first end, and an extension rod extending from the second end of the yoke;
   positioning the extension rod substantially parallel to the elongated rod;
   connecting the extension clamp to the elongated rod by engaging the first and second rod engaging portions of the yoke with the elongated rod and securing first and second set screws extending through the first and second rod engaging portions, respectively, to the elongated rod; and
   attaching a fastener to another portion of the spine by positioning the fastener within the channel of the yoke between the first and second rod engaging portions.

2. The method of claim 1, wherein, once connected, the first and second rod engaging portions circumferentially contact first and second portions of the elongated rod, respectively.

3. The method of claim 1, wherein the first and second set screws extend through an upper surface of the first and second rod engaging portions, respectively.

4. The method of claim 1, wherein the first and second rod engaging portions are hook type elements.

5. The method of claim 1, wherein the extension rod is configured and dimensioned to be captured and retained within a second fastener.

6. The method of claim 1, wherein the extension rod is integrated with the yoke.

7. The method of claim 6, wherein the integrated extension rod and yoke are a monolithic structure.

8. The method of claim 1, wherein, once connected, the elongated rod is offset with the extension rod.

9. The method of claim 1, wherein the fastener is attached to a pedicle.

10. A method of connecting to an original spinal implant including an elongated rod attached to a portion of the spine without removing the original spinal implant, the method comprising:
    providing an extension clamp including a monolithic yoke having a first end and a second end, the first end comprising first and second rod engaging portions and a channel between the first and second rod engaging portions, the second end being spaced apart from the first end, and an extension rod integrated with and extending from the yoke;
    connecting the extension clamp to the elongated rod by engaging the first and second rod engaging portions with the elongated rod and securing first and second set screws extending through the first and second rod engaging portions, respectively, to the elongated rod; and
    attaching a fastener to a portion of the spine by positioning the fastener within the channel of the yoke between the first and second rod engaging portions.

11. The method of claim 10, wherein the integrated extension rod is positioned substantially parallel with the elongated rod before the extension clamp is connected to the elongated rod.

12. The method of claim 11, wherein the integrated extension rod is configured and dimensioned to be captured and retained within a second fastener.

13. The method of claim 12, wherein the first and second fasteners are bone anchors.

14. The method of claim 10, wherein, once connected, the elongated rod is offset with the integrated extension rod.

\* \* \* \* \*